United States Patent
Furuta et al.

(10) Patent No.: US 9,206,096 B2
(45) Date of Patent: Dec. 8, 2015

(54) PROCESS FOR PRODUCING 2, 3, 3, 3-TETRAFLUOROPROPENE

(71) Applicant: ASAHI GLASS COMPANY, LIMITED, Chiyoda-ku (JP)

(72) Inventors: Shoji Furuta, Tokyo (JP); Yu Takeuchi, Tokyo (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 14/486,125

(22) Filed: Sep. 15, 2014

(65) Prior Publication Data
US 2015/0005537 A1 Jan. 1, 2015

Related U.S. Application Data

(63) Continuation of application No. PCT/JP2013/057257, filed on Mar. 14, 2013.

(30) Foreign Application Priority Data

Mar. 14, 2012 (JP) ................. 2012-057568
Jul. 31, 2012 (JP) ................. 2012-169497

(51) Int. Cl.
*C07C 17/269* (2006.01)

(52) U.S. Cl.
CPC .................... *C07C 17/269* (2013.01)

(58) Field of Classification Search
CPC ............................ C07C 17/269; C07C 17/25
USPC ....................................... 570/159
See application file for complete search history.

(56) References Cited

U.S. PATENT DOCUMENTS 2,931,840 A     4/1960    Marquis et al.

FOREIGN PATENT DOCUMENTS

| CN | 101913989 A | 12/2010 |
|----|-------------|---------|
| CN | 102675038   | 9/2012  |
| GB | 904022      | 7/1959  |
| JP | 2007-514747 | 6/2007  |
| JP | 40-2132     | 2/2011  |

OTHER PUBLICATIONS

Yu et al, Chemosphere, 2007, 68(10), 2003-2006.*
U.S. Appl. No. 14/486,143, filed Sep. 15, 2014, Furuta, et al.
U.S. Appl. No. 14/498,153, filed Sep. 26, 2014, Furuta, et al.
International Search Report issued Jun. 18, 2013 in PCT/JP2013/057257 filed Mar. 14, 2013.

* cited by examiner

*Primary Examiner* — Shailendra Kumar
(74) *Attorney, Agent, or Firm* — Oblon, McClelland, Maier & Neustadt, L.L.P.

(57) ABSTRACT

To provide an economically advantageous process for producing industrially useful HFO-1234yf efficiently and in a sufficiently controlled state by one reaction involving thermal decomposition, by using readily available raw material. A process for producing 2,3,3,3-tetrafluoropropene from a raw material composition containing chlorodifluoromethane and chloromethane, by a synthetic reaction involving thermal decomposition, which comprises (a) a step of supplying the chlorodifluoromethane and the chloromethane to a reactor, as preliminarily mixed or separately, in such amounts that the chloromethane would be in a ratio of from 0.01 to 3 mol to 1 mol of the chlorodifluoromethane, (b) a step of supplying a heat medium to the reactor, and (c) a step of bringing the heat medium in contact with the chlorodifluoromethane and the chloromethane in the reactor to form the 2,3,3,3-tetrafluoropropene.

15 Claims, 2 Drawing Sheets

PROCESS FOR PRODUCING 2, 3, 3, 3-TETRAFLUOROPROPENE

This application is a CON of PCT/JP2013/057257, filed Mar. 14, 2013.

TECHNICAL FIELD

The present invention relates to a process for producing 2,3,3,3-tetrafluoropropene, particularly to a process for producing 2,3,3,3-tetrafluoropropene by one reaction from chlorodifluoromethane and chloromethane as raw material.

BACKGROUND ART

In recent years, 2,3,3,3-tetrafluoropropene (HFO-1234yf) has attracted attention as a new refrigerant to replace 1,1,1,2-tetrafluoroethane (HFC-134a) which is a greenhouse gas. In this specification, with respect to a halogenated hydrocarbon, after its chemical name, an abbreviated name of the compound is shown in brackets, and in this specification, as the case requires, instead of the chemical name, its abbreviated name is used.

As a process for producing HFO-1234yf, for example, a process is known wherein 1,1-dichloro-2,2,3,3,3-pentafluoropropane (HCFC-225ca) is subjected to dehydrofluorination with an aqueous alkaline solution in the presence of a phase-transfer catalyst to obtain 1,1-dichloro-2,3,3,3-tetrafluoropropene (CFO-1214ya), which is then used as synthetic raw material and reduced by hydrogen to obtain HFO-1234yf.

However, this process has problems such that it requires multistage reactions whereby installation costs tend to be high, and distillation/purification of the intermediate product and the final product is difficult.

Patent Document 1 discloses that different types of hydrochlorocarbon compounds (e.g. chloromethane and chlorodifluoromethane) are combined and heated at 845±5° C. in the presence of steam for dehydrochlorination and condensation, whereby fluorine atom-containing olefins such as HFO-1234yf and 1,1-difluoroethylene (VdF) are formed.

Further, Patent Document 2 discloses a method for obtaining HFO-1234yf by heating and decomposing a mixture of chloromethane and chlorodifluoromethane or tetrafluoroethylene at a temperature of from 700 to 950° C. by a common heating means such as an electric heater in a reactor.

However, in the method disclosed in Patent Document 2, as the retention time increases, formation of high boiling products as by-products and carbonization of raw material are likely to occur whereby the reactor is likely to get blocked, and by the influence of an acid component formed as a byproduct, a special corrosion resistant apparatus (such as a reaction tube lined with platinum) is required, and thus, in consideration of the industrial production, such a method is totally unrealistic.

In the method disclosed in Patent Document 1, the raw material component was not sufficiently subjected to the reaction. For example, the conversion of chloromethane was 17%, and thus, an efficient reaction was not attained. Further, the proportion of VdF in the obtained product was high, whereby it was difficult to say that HFO-1234yf was efficiently produced.

PRIOR ART DOCUMENTS

Patent Documents

Patent Document 1: JP-B-40-2132 (Example 4)
Patent Document 2: U.S. Pat. No. 2,931,840

DISCLOSURE OF INVENTION

Technical Problem

The present invention has been made in view of the above situations and has an object to provide an economically advantageous process for producing industrially useful HFO-1234yf efficiently and in a sufficiently controlled state by one reaction involving thermal decomposition, by using readily available raw material.

Solution to Problem

The present invention provides a process for producing 2,3,3,3-tetrafluoropropene (HFO-1234yf) from chlorodifluoromethane (R22) and chloromethane (R40), which comprises (a) a step of supplying the R22 and the R40 to a reactor, as preliminarily mixed or separately, in such amounts that the R40 would be in a ratio of from 0.01 to 3 mol to 1 mol of the R22, (b) a step of supplying a heat medium to the reactor, and (c) a step of bringing the heat medium in contact with the R22 and the R40 in the reactor to form the HFO-1234yf.

Advantageous Effects of Invention

According to the process of the present invention, an industrially useful HFO-1234yf can be efficiently produced by using readily available R22 and R40 as raw material and reacting them as they are without taking out an intermediate product from the reaction system. Accordingly, as compared with conventional methods for producing HFO-1234yf, it is possible to substantially reduce the costs required for the raw material and production facilities.

Further, according to the process of the present invention, control of the production (reaction) conditions is easy, and thus quantitative production of HFO-1234yf becomes possible, whereby economical merits become substantial. Specifically, it is economically advantageous that in the synthetic reaction involving thermal decomposition using R22 and R40 as raw material, the proportion of HFO-1234yf in the reaction mixture can be made at least a certain value in the relative relation to VdF, the content ratio of which tends to be high in the reaction mixture. Further, recycling of byproducts is possible, whereby economical effects are substantial.

DESCRIPTION OF EMBODIMENTS

Figure 1:
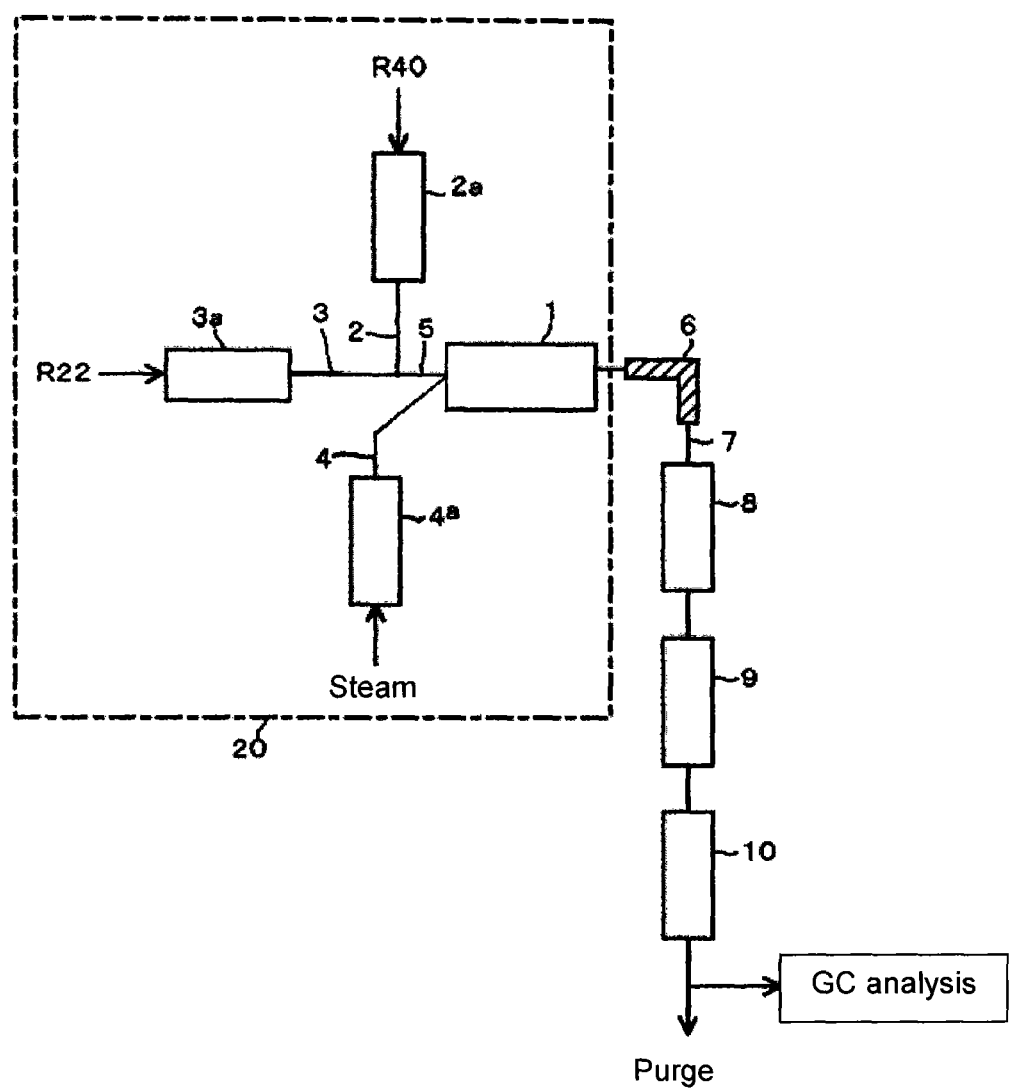
FIG. 1 is a view illustrating an example of a reaction apparatus to be used in the process of the present invention.

Now, embodiments of the present invention will be described.

The present invention provides a process for producing HFO-1234yf by a synthetic reaction involving thermal decomposition in the presence of a heat medium by using chlorodifluoromethane (R22) and chloromethane (R40) as raw material. And, this process comprises (a) a step of supplying the R22 and the R40 to a reactor, as preliminarily mixed or separately, in such amounts that the R40 would be in a ratio of from 0.01 to 3 mol to 1 mol of the R22, (b) a step of supplying a heat medium to the reactor, and (c) a step of bringing the heat medium in contact with the R22 and the R40 in the reactor.

The process of the present invention may be a continuous system process or a batch system process. In the continuous system process, the supply of R22 and R40 to the reactor in the above ratio, the supply of the heat medium to the reactor and the withdrawal of the reaction mixture containing HFO-1234yf from the reactor are continuously conducted, respectively. In the batch system production, either one of the supply of R22 and R40 in the step (a) and the supply of a heat medium in the step (b) may precede the other, or they may be conducted simultaneously. That is, even in a case where at the time of supplying either one of the raw material and the heat medium first, the other is not supplied to the reactor, the component to be supplied later may be supplied during the retention of the raw material or the heat medium supplied first, so that the raw material and the heat medium will be contacted with each other for a predetermined time in the reactor.

From the viewpoint of the production efficiency, the process of the present invention is preferably a continuous system process. In the following, the process of the present invention will be described with reference to an embodiment wherein it is applied to a continuous system production, but it should be understood that the present invention is by no means limited thereto.

Further, a step of withdrawing a reaction mixture containing HFO-1234yf from the reactor will hereinafter be referred to as the step (d). Therefore, in the continuous process, the steps (a), (b) and (d) are all conducted simultaneously.

<Synthetic Reaction of R22 and R40>

In the process of the present invention, the main reaction in the reactor is represented by the following formula (1).

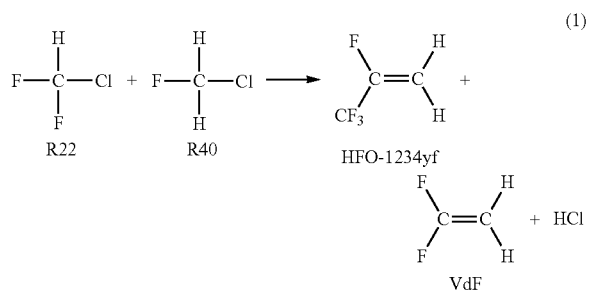

It is considered that raw material R22 and R40 undergo a thermal decomposition and dehydrochlorination reaction to form a mixture containing difluorocarbene (F2C:) and R40, and further, they are converted, directly by an addition reaction or via at least one type of intermediate, to tetrafluoropropene, particularly to HFO-1234yf. In this invention, from such a thermal decomposition reaction to the HFO-1234yf-forming reaction will be referred to as a synthetic reaction involving thermal decomposition.

Here, as shown in the above formula (1), as a byproduct, mainly VdF is formed in the reactor. Further, depending upon the reaction conditions, other byproducts as will be described later, may be formed in certain amounts in addition to VdF, but in the above formula (1), only VdF being the most typical byproduct is shown.

<Raw Material>

In the process for producing HFO-1234yf of the present invention, R22 and R40 are used as raw material.

The molar ratio of the supply amount of R40 to the supply amount of R22 to be supplied to the reactor (i.e. R40/R22 where the supply molar amount of R22 and the supply molar amount of R40 are represented by R22 and R40, respectively) is from 0.01 to 3. Here, in this embodiment wherein the raw material and the heat medium are permitted to continuously flow in the reactor for the reaction, the supply amounts of the respective components of the raw material and the heat medium are deemed to represent the supply amounts per unit time. Further, the molar ratio R40/R22 is more preferably within a range of from 0.1 to 3, particularly preferably within a range of from 0.1 to 1.5.

By adjusting the molar ratio R40/R22 to be within such a range, the conversion of the raw material components, particularly the conversion of R40 can be made high. Further, the proportion of HFO-1234yf in the reaction mixture withdrawn from the reactor can be made high as a relative proportion to VdF. Specifically, the content ratio of HFO-1234yf to VdF in the reaction mixture withdrawn from the reactor can be made to be at least 0.14 by molar ratio as the molar amount of HFO-1234yf/the molar amount of VdF (hereinafter represented by "HFO-1234yf/VdF"). The molar ratio HFO-1234yf/Vdf is preferably at least 0.17, more preferably at least 0.20. When the value of the molar ratio HFO-1234yf/VdF is at least 0.14, such a process may be regarded as having an economical superiority as a process for producing HFO-1234yf.

As the raw material, in addition to such two components, it is possible to use a fluorinated compound (other than R22) capable of forming F2C: by thermal decomposition in the reactor, such as VdF, tetrafluoroethylene (TFE), hexafluoropropene (HFP), octafluorocyclobutane (RC318), chlorotrifluoroethylene (CTFE), trifluoroethylene, or hexafluoropropylene oxide (HFPO). In a case where such a fluorinated compound capable of forming F2C: by thermal decomposition in the reactor, is further used as a raw material component, a fluorinated compound freshly prepared may be used. However, from the viewpoint of recycling, it is preferred to use at least one member selected from fluorinated compounds formed as byproducts in the above-mentioned synthetic reaction involving thermal decomposition, including e.g. VdF, TFE, HFP, RC318, CTFE, trifluoroethylene, etc.

In the following, the fluorinated compound capable of forming F2C: by thermal decomposition in the reactor, other than R22, will be referred to as VdF, etc.

In the process of the present invention, the reaction mixture withdrawn from an outlet of the reactor contains unreacted raw material components, the reaction product, byproducts, the heat medium, etc. Therefrom, the heat medium and the desired product HFO-1234-yf are separated, and further, byproducts other than VdF, etc. are removed, to obtain a mixture which is composed mainly of unreacted raw material R22 and R40, and VdF, etc. By supplying this mixture together with fresh R22 and R40 to the reactor, recycling of VdF, etc. becomes possible, such being economically advantageous.

Each raw material component may be introduced into the reactor at ordinary temperature, but in order to improve the reactivity in the reactor, the temperature at the time of introducing into the reactor may be adjusted by e.g. heating. However, the fluorinated compound capable of forming F2C: such as R22, and R40, are different in the temperature range preferred to improve the reactivity, and therefore, it is preferred to conduct the temperature adjustment separately.

The temperature of R22 to be supplied to the reactor and the temperature of VdF, etc. to be supplied to the reactor, are preferably made to be from 0 to 600° C. with a view to adjusting them to a temperature where carbonization hardly takes place while the reactivity is high to a certain extent.

From the viewpoint of further improving the reactivity, it is preferred to heat R22 and VdF, etc. to at least ordinary temperature (25° C.) and at most 600° C., or more preferred to heat them from 100 to 500° C., before introducing them to the reactor.

Whereas, the temperature of R40 to be supplied to the reactor is preferably made to be from 0 to 1,200° C. from the viewpoint of the reactivity. From the viewpoint of further improving the reactivity, it is preferred to heat R40 to at least ordinary temperature and at most 1,200° C., or more preferred to heat it from 100 to 800° C., before introducing it to the reactor.

However, the temperature of each raw material component to be supplied to the reactor is set to be at most the temperature in the reactor in the step (c) which will be described hereinafter.

The respective raw material components such as R22 and R20 and further VdF, etc. which are used as the case requires, may be supplied to the reactor separately, or the respective components may be mixed and then supplied to the reactor. In a case where the respective components are mixed and then supplied, the raw material components may be divided into groups, e.g. into a group of R22 and VdF, etc. and another group of others, and the respective groups may be mixed and then separately supplied to the reactor, or all raw material components may be mixed and then supplied. When the above-mentioned difference in the temperature conditions is taken into consideration, it is preferred that R22 and VdF, etc. to be used as the case requires, are mixed, adjusted to the above-mentioned preferred temperature condition and then supplied to the reactor, and separately therefrom, R40 is adjusted to the above-mentioned preferred temperature condition and then supplied to the reactor.

Whereas, in a case where the respective raw material components such as R22 and R40 and further, VdF, etc. to be used as the case requires, are preliminarily mixed and then supplied to the reactor, with a view to preventing the reaction/decomposition from proceeding before the reactor, the temperature at the time of introduction to the reactor is adjusted to be preferably lower than 600° C., particularly preferably lower than 500° C.

<Heat Medium>

The heat medium in the present invention is supplied to the reactor so that it will be in contact with the above-mentioned raw material for a certain time in the reactor. The heat medium is a medium which undergoes no thermal decomposition at a temperature in the reactor, and specifically, it is preferably a medium which undergoes no thermal decomposition at a temperature of from 100 to 1,200° C. The heat medium may be at least one member selected from steam, nitrogen and carbon dioxide. It is preferred to use a gas containing steam in an amount of at least 50 vol % and the rest being nitrogen and/or carbon dioxide. In order to remove HCl formed by a thermal decomposition reaction of the above formula (1) in the form of hydrochloric acid, the content ratio of steam in the heat medium is preferably at least 50 vol %, and it is particularly preferred to use a gas consisting substantially solely of steam (100 vol %).

The supply amount of the heat medium is preferably a proportion of from 20 to 98 vol %, more preferably from 50 to 95 vol %, in the total of the supply amounts of the heat medium and the raw material. By adjusting the proportion of the supply amount of the heat medium to be at least 20 vol % to the total of the supply amounts of the heat medium and the raw material, it becomes possible to produce HFO-1234yf efficiently by facilitating the thermal decomposition reaction of the above formula (1) while preventing formation of high-boiling point products or carbonization of the raw material. Whereas, if the proportion exceeds 98 vol %, the productivity lowers substantially, such being industrially not practical.

Further, from the viewpoint of the thermal decomposition and the reactivity of the raw material components, the temperature of the heat medium to be supplied to the reactor is adjusted to be preferably from 100 to 1,200° C. With a view to further improving the reactivity of the raw material components, the temperature of the heat medium to be supplied to the reactor is adjusted to be more preferably from 600 to 900° C., particularly preferably from 700 to 900° C.

The contact time in the reactor, of the heat medium and the raw material thus supplied, is adjusted to be preferably from 0.01 to 10 seconds, more preferably from 0.2 to 3.0 seconds. By adjusting the contact time to be from 0.01 to 10 seconds, it is possible to sufficiently facilitate the reaction to form HFO-1234yf and to prevent formation of byproducts. Here, the contact time of the heat medium and the raw material corresponds to the retention time of the raw material in the reactor and can be controlled by adjusting the supply amount (flow rate) of the raw material to the reactor.

<Reactor>

As the reactor, so long as it is one durable to the after-mentioned temperature and pressure in the reactor, its shape is not particularly limited, and for example, a cylindrical vertical reactor may be mentioned. The material for the reactor may, for example, be glass, iron, nickel or an alloy containing iron and nickel as the main components.

The temperature in the reactor in the step (c) is set to be a temperature of at least the temperature of the respective components constituting the raw material to be supplied to the reactor, i.e. a temperature of at least the temperature of R40, R22 and VdF, etc. to be used as the case requires, and preferably from 400 to 1,200° C., further preferably within a range of from 600 to 900° C., particularly preferably within a range of from 710 to 900° C., most preferably within a range of from 710 to 830° C. By adjusting the temperature in the reactor to be within the range of from 400 to 1,200° C., it is possible to increase the reaction rate of the formation reaction involving thermal decomposition represented by the above formula (1) and to obtain HFO-1234yf efficiently.

The temperature in the reactor can be controlled by adjusting the temperature and pressure of the above heat medium to be supplied to the reactor. Further, it is also possible to supplementarily heat the inside of the reactor by e.g. an electric heater so that the temperature in the reactor becomes to be within the most preferred temperature range (from 710 to 830° C.).

The pressure in the reactor is adjusted to be preferably from 0 to 2.0 MPa, more preferably within a range of from 0 to 0.5 MPa, by gauge pressure.

<Reaction Apparatus>

Figure 2:
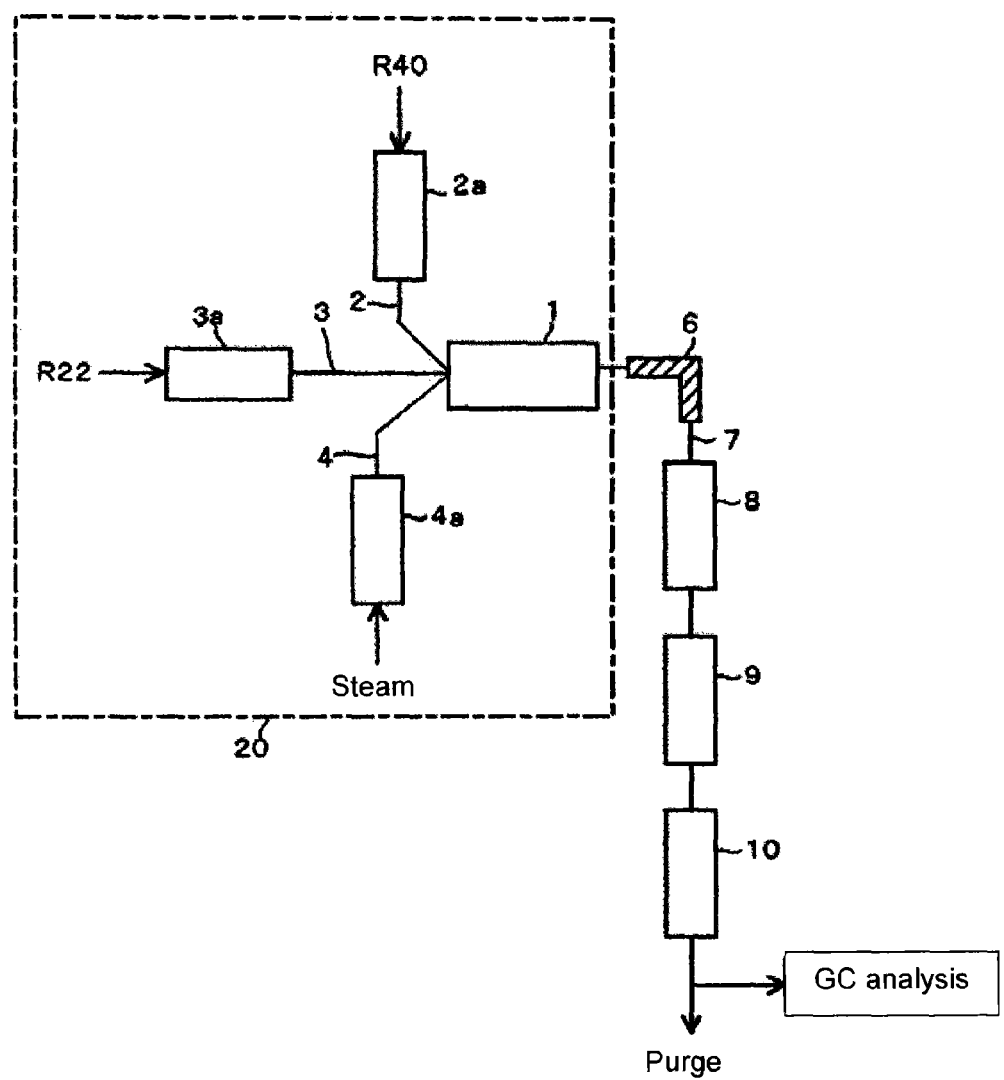
FIG. 2 is a view illustrating another example of a reaction apparatus to be used in the process of the present invention.

Examples of the reaction apparatus to be used for the production of HFO-1234yf in the present invention are shown in FIGS. 1 and 2.

The reaction apparatus 20 has a reactor 1 provided with a heating means such as an electric heater. To the reactor 1, a supply line 2 for R40 as a first raw material component, a supply line 3 for R22 as a second raw material component, and a supply line 4 for steam as a heat medium, are connected as described in the following. Here, provision of the heating means in the reactor 1 is not necessarily required.

In the supply line 2 for R40 and the supply line 3 for R22, preheaters 2a and 3a each provided with an electric heater or the like, are respectively installed, so that the respective raw material components to be supplied, are preheated to predetermined temperatures and then supplied to the reactor 1. Further, in the supply line 4 for steam, a superheated steam generator 4a is installed, whereby the temperature and pressure of steam to be supplied, are adjusted.

These supply lines 2, 3 and 4 may be separately connected to the reactor 1, respectively. Otherwise, some or all of the supply lines may be interlinked prior to the reactor 1 and then connected to the reactor 1.

For example, as shown in FIG. 1, the supply lines 2 and 3 may be interlinked after the respective preheaters 2a and 3a so that the raw material mixture having all raw material components mixed, will be supplied to the reactor 1 from the raw material mixture-supply line 5, and steam will be supplied to the reactor 1 from a steam-supply line 4 separately from the raw material mixture-supplying line 5.

Otherwise, as shown in FIG. 2, the supply line 2 for R40, the supply line 3 for R22 and the supply line 4 for steam may be separately connected to the reactor 1, respectively, so that R40, R22 and stream will be separately supplied to the reactor 1, and they will be integrally mixed in the vicinity of the inlet of the reactor 1.

To the outlet of the reactor 1, an outlet line 7 having a cooling means 6 such as a water chiller installed, is connected. In the outlet line 7, further, a steam and acidic liquid-recovery tank 8, an alkaline cleaning device 9 and a dehydrating tower 10 are sequentially installed. And, it is so designed that after dehydration by the dehydrating tower 10, the respective components in the obtained gas are analyzed and quantified by an analytical device such as gas chromatography (GC).

Here, a gas obtained by withdrawing the reaction mixture containing HFO-1234yf from the reactor and removing an acidic substance such as hydrogen chloride, steam, water, etc. by the above-mentioned treatments in the outlet line 7, will be hereinafter referred to as outlet gas.

<Outlet Gas Components>

In the process of the present invention, HFO-1234yf is obtainable as a component of the above outlet gas. Compounds other than HFO-1234yf contained in the outlet gas may, for example, be methane, ethylene, VdF, TFE, HFP, CTFE, trifluoroethylene, RC318, 1,3,3,3-tetrafluoropropene (HFO-1234ze), 1,2-difluoroethylene, etc.

Among these components, methane and ethylene having a methylene group ($=CH_2$) or a methyl group ($—CH_3$) are compounds derived from raw material component R40, and VdF, TFE, HFP, CTFE, trifluoroethylene, RC318, HFO-1234ze and 1,2-difluoroethylene having fluorine atoms are, respectively, compounds derived from raw material component R22. Further, HFO-1234yf and VdF as well as HFO-1234ze and 1,2-difluoroethylene, are compounds derived from R22 and also compounds derived from R40.

The above components other than HFO-1234yf contained in the outlet gas can be removed to a desired extent by a known means such as distillation, etc. And, separated VdF, TFE, HFP, CTFE, trifluoroethylene and RC318 are compounds capable of forming $F_2C$: and may be recycled as a part of raw material. Further, obtained VdF, TFE, CTFE, etc. may be used as raw material for e.g. PVdF (VdF polymer), PTFE (TFE polymer), FEP (TFE-HFP copolymer), VdF-HFP copolymer, PCTFE (CTFE polymer), ECTFE (ethylene-CTFE copolymer), etc., as the case requires.

According to the process of the present invention, it is possible to efficiently produce HFO-1234yf useful as a new refrigerant with a global warming potential (GWP) being as small as 4, by one reaction using R22 and R40 as raw material. For example, according to the process of the present invention, as compared with a method which requires a multi-stage reaction to produce HFO-1234yf via CFO-1214ya using HCFC-225ca as raw material, it is possible not only to reduce costs required for the raw material and production facilities but also to substantially reduce the energy required for the production.

Further, according to the process of the present invention, a heat medium is used, whereby control of the production (reaction) conditions, particularly control of the temperature conditions, is easy, and accordingly, quantitative production of HFO-1234yf becomes possible, whereby economical merits are substantial. Specifically, it is economically advantageous that in the synthetic reaction involving thermal decomposition using R22 and R40 as raw material, the proportion of HFO-1234yf in the reaction mixture can be made to be at least a certain level, in a relative relation to VdF, of which the content ratio tends to be high in the reaction mixture, e.g. the content ratio of HFO-1234yf to VdF in the reaction mixture can be made to be at least 0.14 as a molar ratio of HFO-1234yf/VdF. Furthermore, byproducts capable of forming $F_2C$: may be used as raw material components by recycling, and economical effects are thereby substantial.

EXAMPLES

Now, the present invention will be described in further detail with reference to Examples, but it should be understood that the present invention is by no means restricted by these Examples.

Example 1

Using the reaction apparatus as shown in FIG. 1, from a raw material gas comprising R22 and R40, crude HFO-1234yf was obtained as follows.

Into a stainless steel tube preheater 2a in an electric furnace set at an internal temperature of 500° C., R40 was continuously introduced, and R40 was heated to 500° C. Further, into a stainless steel tube preheater 3a in an electric furnace set at an internal temperature of 500° C., R22 was continuously introduced, and R22 was heated to 500° C.

Steam (water vapor) heated by a heated-steam generator 4a as an electric furnace set at an internal temperature of 850° C. was supplied to the reactor 1 controlled to have an internal temperature of 850° C. under 0.04 MPa. Further, the raw material gas components (R40 and R22) preheated and adjusted to the above temperature were supplied to the reactor 1 so that the molar ratio of the supply amounts of the raw material components would be R40/R22=1.5, and the supply proportion of steam to the entire gas supply amount (the proportion represented by a volume ratio of steam/(R40+R22+ steam)) would be 87 vol %. Here, the reactor 1 was controlled to have an internal pressure (gauge pressure) of 0.04 MPa and an internal temperature of 850° C. Hereinafter, the pressure will be a gauge pressure in each case.

Thus, the flow rate of the raw material gas (the supply amount per unit time) was controlled so that the retention time of the raw material gas in the reactor would be 1 second, and the gas of the reaction mixture was withdrawn from the outlet of the reactor. The measured value of the internal temperature of the reactor was 850° C., and the measured value of the internal pressure of the reactor was 0.042 MPa. Here, the gas of the reaction mixture withdrawn from the outlet of the reactor contains unreacted raw material gas in addition to the gas formed by the reaction or by side reactions.

Then, the gas of the reaction mixture withdrawn from the outlet of the reactor was cooled to at most 100° C. and subjected to recovery of steam and the acidic liquid and alkaline cleaning sequentially and then to dehydration treatment, whereupon the obtained outlet gas was analyzed by gas chromatography, and the molar composition of the gas components contained in the outlet gas was calculated. These results are shown in Table 1 together with the reaction conditions.

Here, the preheat temperatures of R40 and R22 are preset temperatures in the respective electric furnaces for preheating, and the steam temperature is a preset temperature in the electric furnace for heating steam. Further, the steam pressure is a preset pressure.

Further, based on the molar composition of the outlet gas obtained by the analysis by gas chromatography, the molar ratio of HFO-1234yf to VdF in the outlet gas, i.e. HFO-1234yf/VdF, was calculated. Further, the yield and conversion (reaction rate) of R40, the yield and selectivity of each component derived from R40, the yield and conversion (reaction rate) of R22, and the yield and selectivity of each component derived from R22, were obtained, respectively. These results are shown in the lower columns in Table 1.

The above values have the following meanings, respectively.

(R40 Yield)

The proportion (mol %) which R40 occupies among R40-derived components (components having a methylene group or a methyl group) in the outlet gas.

(R40 Conversion (Reaction Rate))

When the proportion which R40 occupies among R40-derived components (i.e. R40 yield) is X %, (100−X) % is referred to as the conversion (reaction rate) of R40. It means the proportion (mol %) of reacted R40.

(Yield of Each Component Derived from R40)

The proportion (mol %) which each compound other than R40 occupies among R40-derived components in the outlet gas.

(Selectivity of Each Component Derived from R40)

In reacted R40, % of one converted to each component other than R40. The selectivity of each component is obtainable by [yield of each component derived from R40]/[conversion (reaction rate) of R40].

(R22 Yield)

The proportion (mol %) which R22 occupies among R22-derived components (components having fluorine atoms) in the outlet gas.

(R22 Conversion (Reaction Rate))

When the proportion which R22 occupies among R22-derived components (i.e. R22 yield) is X %, (100−X) % is referred to as the conversion (reaction rate) of R22. It means the proportion (mol %) of reacted R22.

(Yield of Each Component Derived from R22)

The proportion (mol %) which each compound other than R22 occupies among R22-derived components in the outlet gas.

(Selectivity of Each Component Derived from R22)

In reacted R22, % of one converted to each component other than R22. The selectivity of each component is obtainable by [yield of each component derived from R22]/[conversion (reaction rate) of R22].

(HFO-1234yf/VdF)

The proportion (molar ratio) of HFO-1234yf to VdF in the outlet gas.

It is obtainable by [mol % of HFO-1234yf in the outlet gas]/[mol % of VdF in the outlet gas]. It shows in what proportion (molar ratio), HFO-1234yf is present to VdF in the outlet gas.

Examples 2 to 4

The reaction was conducted under the same conditions as in Example 1 except that the molar ratio (R40/R22) of the supply amount of R40 to the supply amount of R22 was changed as shown in Table 1. Then, the gas of a reaction mixture withdrawn from the outlet of the reactor was treated in the same manner as in Example 1, and then, the obtained outlet gas was analyzed in the same manner as in Example 1. The results are shown in Table 1 together with the reaction conditions.

Comparative Examples 1 and 2

The reaction was conducted under the same conditions as in Example 1 except that the molar ratio (R40/R22) of the supply amount of R40 to the supply amount of R22 was changed to 4 (Comparative Example 1) or 5 (Comparative Example 2). Then, the gas of a reaction mixture withdrawn from the outlet of the reactor was treated in the same manner as in Example 1, and then, the obtained outlet gas was analyzed in the same manner as in Example 1. The results are shown in Table 1 together with the reaction conditions.

TABLE 1

| | | | Example No. | | | | | |
|---|---|---|---|---|---|---|---|---|
| | | | Ex. 1 | Ex. 2 | Ex. 3 | Ex. 4 | Comp. Ex. 1 | Comp. Ex. 2 |
| Production conditions | Temperature (° C.) in reactor | | 850 | 850 | 850 | 850 | 850 | 850 |
| | Pressure (gauge pressure) (MPa) | | 0.042 | 0.042 | 0.042 | 0.042 | 0.042 | 0.042 |
| | Retention time (s) | | 1.0 | 1.0 | 1.0 | 1.0 | 1.0 | 1.0 |
| | R40/R22 (molar ratio) | | 1.5 | 0.5 | 0.25 | 0.1 | 4.0 | 5.0 |
| | R40 temperature (° C.) | | 500 | 500 | 500 | 500 | 500 | 500 |
| | R22 temperature (° C.) | | 500 | 500 | 500 | 500 | 500 | 500 |
| | Heat medium (steam)/ (R40 + R22 + steam) × 100 (vol %) | | 87 | 87 | 87 | 87 | 87 | 87 |
| | Heat medium temperature (° C.) | | 850 | 850 | 850 | 850 | 850 | 850 |
| | Heat medium pressure (gauge pressure) (MPa) | | 0.042 | 0.042 | 0.042 | 0.042 | 0.042 | 0.042 |
| Analytical results of reaction gas | Molar composition of outlet gas (mol %) | TFE | 0.23 | 2.24 | 6.05 | 8.91 | 0.08 | 1.36 |
| | | VdF | 49.29 | 59.08 | 40.42 | 22.26 | 26.38 | 22.96 |
| | | HFP | 0.27 | 1.55 | 4.93 | 10.67 | 0.08 | 0.09 |
| | | Trifluoroethylene | 0.79 | 3.81 | 6.50 | 9.43 | 0.27 | 0.23 |
| | | RC318 | 0.01 | 0.00 | 0.00 | 0.00 | 0.08 | 0.03 |
| | | HFO-1234yf | 6.88 | 10.48 | 9.08 | 5.08 | 3.10 | 2.64 |
| | | R22 | 0.25 | 1.80 | 4.05 | 6.17 | 0.07 | 0.35 |
| | | CTFE | 0.32 | 1.10 | 2.07 | 3.08 | 0.08 | 0.08 |

TABLE 1-continued

| | | Example No. | | | | | |
|---|---|---|---|---|---|---|---|
| | | Ex. 1 | Ex. 2 | Ex. 3 | Ex. 4 | Comp. Ex. 1 | Comp. Ex. 2 |
| | R40 | 33.99 | 8.30 | 4.40 | 3.77 | 61.36 | 64.78 |
| | Others | 7.96 | 11.63 | 22.51 | 30.65 | 8.51 | 7.48 |
| | Total | 100.0 | 100.0 | 100.0 | 100.0 | 100.0 | 100.0 |
| | HFO-1234yf/VdF | 0.140 | 0.177 | 0.225 | 0.228 | 0.117 | 0.115 |
| R40 yield (%) | | 35.23 | 9.85 | 6.74 | 8.78 | 61.69 | 66.56 |
| R40 conversion (=R40 reaction rate (%)) | | 64.77 | 90.15 | 93.26 | 91.22 | 38.31 | 33.44 |
| R40-derived yield (%) | HFO-1234yf | 7.13 | 12.44 | 13.90 | 11.84 | 3.11 | 2.71 |
| | VdF | 51.09 | 70.14 | 61.92 | 51.89 | 26.52 | 23.58 |
| | Others | 6.55 | 7.57 | 17.45 | 27.50 | 8.68 | 7.15 |
| R40-derived selectivity (%) | HFO-1234yf | 11.01 | 13.80 | 14.91 | 12.98 | 8.12 | 8.12 |
| | VdF | 78.88 | 77.80 | 66.39 | 56.88 | 69.22 | 70.51 |
| | Others | 10.11 | 8.39 | 18.71 | 30.15 | 22.66 | 21.37 |
| R22 yield (%) | | 0.33 | 1.47 | 2.67 | 3.44 | 0.17 | 0.93 |
| R22 conversion (=R22 reaction rate (%)) | | 99.67 | 98.53 | 97.33 | 96.56 | 99.83 | 99.07 |
| R22-derived yield (%) | TFE | 0.61 | 3.68 | 7.97 | 9.95 | 0.38 | 7.28 |
| | HFO-1234yf | 18.07 | 17.17 | 11.97 | 5.67 | 15.50 | 14.13 |
| | VdF | 64.74 | 48.40 | 26.66 | 12.44 | 66.06 | 61.37 |
| | HFP | 1.08 | 3.81 | 9.75 | 17.88 | 0.59 | 0.74 |
| | Trifluoroethylene | 2.08 | 6.25 | 8.57 | 10.53 | 1.36 | 1.24 |
| | CTFE | 0.83 | 1.81 | 2.73 | 3.44 | 0.38 | 0.40 |
| | RC318 | 0.04 | 0.00 | 0.00 | 0.00 | 0.78 | 0.28 |
| | Others | 12.23 | 17.41 | 29.67 | 36.65 | 14.78 | 13.63 |
| R22-derived selectivity (%) | TFE | 0.61 | 3.73 | 8.19 | 10.31 | 0.38 | 7.35 |
| | HFO-1234yf | 18.13 | 17.43 | 12.30 | 5.88 | 15.53 | 14.26 |
| | VdF | 64.95 | 49.12 | 27.39 | 12.88 | 66.17 | 61.95 |
| | HFP | 1.08 | 3.87 | 10.02 | 18.52 | 0.59 | 0.75 |
| | Trifluoroethylene | 2.08 | 6.34 | 8.81 | 10.91 | 1.37 | 1.25 |
| | CTFE | 0.83 | 1.83 | 2.80 | 3.56 | 0.38 | 0.41 |
| | RC318 | 0.04 | 0.00 | 0.00 | 0.00 | 0.78 | 0.28 |
| | Others | 12.27 | 17.67 | 30.49 | 37.95 | 14.80 | 13.76 |

Example 5

In the same manner as in Example 1, using the apparatus as shown in FIG. 2, from raw material gas comprising R22 and R40, crude HFO-1234yf was obtained as follows.

Into a stainless steel tube in an electric furnace set at an internal temperature of 600° C., R40 was continuously introduced, and R40 was heated to 600° C. Further, into a stainless steel tube in an electric furnace set at an internal temperature of 300° C., R22 was continuously introduced, and R22 was heated to 300° C.

These raw material gas components (R40 and R22) preheated and adjusted to the above temperatures, and steam (water vapor) heated by an electric furnace set at an internal temperature of 750° C., were adjusted so that the molar ratio of the supply amounts of the raw material components would be R40/R22=3, and the supply proportion of steam to the entire gas supply amount (i.e. the proportion represented by a volume ratio of steam/(R40+R22+ steam)) would be 90 vol %, and supplied to a reactor controlled to have an internal pressure of 0.04 and an internal temperature of 800° C.

Thus, the flow rate of the raw material gas (the supply amount per unit time) was controlled so that the retention time of the raw material gas in the reactor would be 0.5 second, and the gas of the reaction mixture was withdrawn from the outlet of the reactor. The measured value of the internal temperature of the reactor was 800° C., and the measured value of the internal pressure of the reactor was 0.042 MPa. Then, the gas of the reaction mixture withdrawn from the outlet of the reactor was treated in the same manner as in Example 1, whereupon the obtained outlet gas was analyzed in the same manner as in Example 1. The results are shown in Table 2 together with the reaction conditions.

Examples 6 to 11

The reaction was conducted under the same conditions as in Example 5 except that the molar ratio (R40/R22) of the supply amount of R40 to the supply amount of R22 was changed as shown in Table 2. Then, the gas of a reaction mixture withdrawn from the outlet of the reactor was treated in the same manner as in Example 1, and then, the obtained outlet gas was analyzed in the same manner as in Example 1. The results are shown in Table 2 together with the reaction conditions.

Comparative Example 3

The reaction was conducted under the same conditions as in Example 5 except that the molar ratio (R40/R22) of the supply amount of R40 to the supply amount of R22 was changed to 10. Then, the gas of a reaction mixture withdrawn from the outlet of the reactor was treated in the same manner as in Example 1, and then, the obtained outlet gas was analyzed in the same manner as in Example 1. The results are shown in Table 2 together with the reaction conditions.

TABLE 2

|  |  | Example No. | | | | | | | |
|---|---|---|---|---|---|---|---|---|---|
|  |  | Ex. 5 | Ex. 6 | Ex. 7 | Ex. 8 | Ex. 9 | Ex. 10 | Ex. 11 | Comp. Ex. 3 |
| Production conditions | Temperature (° C.) in reactor | 800 | 800 | 800 | 800 | 800 | 800 | 800 | 800 |
|  | Pressure (gauge pressure) (MPa) | 0.042 | 0.042 | 0.042 | 0.042 | 0.042 | 0.042 | 0.042 | 0.042 |
|  | Retention time (s) | 0.5 | 0.5 | 0.5 | 0.5 | 0.5 | 0.5 | 0.5 | 0.5 |
|  | R40/R22 (molar ratio) | 3.0 | 2.0 | 1.3 | 0.5 | 0.4 | 0.3 | 0.1 | 10.0 |
|  | R40 temperature (° C.) | 600 | 600 | 600 | 600 | 600 | 600 | 600 | 600 |
|  | R22 temperature (° C.) | 300 | 300 | 300 | 300 | 300 | 300 | 300 | 300 |
|  | Heat medium (steam)/ (R40 + R22 + steam) × 100 (vol %) | 90 | 90 | 90 | 90 | 90 | 90 | 90 | 90 |
|  | Heat medium temperature (° C.) | 750 | 750 | 750 | 750 | 750 | 750 | 750 | 750 |
|  | Heat medium pressure (gauge pressure) (MPa) | 0.042 | 0.042 | 0.042 | 0.042 | 0.042 | 0.042 | 0.042 | 0.042 |
| Analytical results of reaction gas | Molar composition of outlet gas (mol %)p | TFE | 8.146 | 11.94 | 16.47 | 31.68 | 31.50 | 39.22 | 52.64 | 2.45 |
|  |  | VdF | 12.245 | 16.08 | 18.05 | 16.02 | 17.62 | 15.85 | 10.50 | 6.69 |
|  |  | HFP | 0.136 | 0.22 | 0.30 | 0.62 | 0.69 | 0.79 | 1.38 | 0.00 |
|  |  | Trifluoroethylene | 0.298 | 0.29 | 0.26 | 0.20 | 0.26 | 0.25 | 0.32 | 0.09 |
|  |  | RC318 | 0.063 | 0.12 | 0.20 | 0.59 | 0.61 | 0.79 | 1.29 | 0.01 |
|  |  | HFO-1234yf | 2.523 | 3.54 | 4.32 | 4.80 | 5.06 | 4.93 | 3.42 | 0.86 |
|  |  | R22 | 0.869 | 1.89 | 2.60 | 4.00 | 3.28 | 6.11 | 7.39 | 1.69 |
|  |  | CTFE | 0.127 | 0.22 | 0.30 | 0.52 | 0.58 | 0.63 | 0.81 | 0.04 |
|  |  | R40 | 65.076 | 58.85 | 53.12 | 39.63 | 37.97 | 29.25 | 19.86 | 82.54 |
|  |  | Others | 10.516 | 6.84 | 4.36 | 1.93 | 2.43 | 2.19 | 2.40 | 5.63 |
|  |  | Total | 100.0 | 100.0 | 100.0 | 100.0 | 100.0 | 100.0 | 100.0 | 100.0 |
|  |  | HFO-1234yf/VdF | 0.206 | 0.220 | 0.240 | 0.299 | 0.287 | 0.311 | 0.326 | 0.128 |
|  | R40 yield (%) |  | 71.93 | 69.43 | 67.06 | 64.58 | 61.25 | 57.38 | 57.46 | 86.31 |
|  | R40 conversion (=R40 reaction rate (%)) |  | 28.07 | 30.57 | 32.94 | 35.42 | 38.75 | 42.62 | 42.54 | 13.69 |
|  | R40-derived yield (%) | HFO-1234yf | 2.79 | 4.18 | 5.46 | 7.82 | 8.16 | 9.66 | 9.90 | 0.90 |
|  |  | VdF | 13.53 | 18.97 | 22.78 | 26.12 | 28.42 | 31.08 | 30.38 | 7.00 |
|  |  | Others | 11.75 | 7.42 | 4.69 | 1.48 | 2.17 | 1.88 | 2.26 | 5.79 |
|  | R40-derived selectivity (%) | HFO-1234yf | 9.93 | 13.66 | 16.58 | 22.09 | 21.07 | 22.66 | 23.27 | 6.57 |
|  |  | VdF | 48.21 | 62.07 | 69.18 | 73.74 | 73.34 | 72.93 | 71.42 | 51.12 |
|  |  | Others | 41.86 | 24.26 | 14.25 | 4.17 | 5.59 | 4.41 | 5.31 | 42.32 |
|  | R22 yield (%) |  | 2.35 | 3.58 | 3.85 | 3.95 | 3.17 | 5.03 | 5.05 | 10.10 |
|  | R22 conversion (=R22 reaction rate (%)) |  | 97.65 | 96.42 | 96.15 | 96.05 | 96.83 | 94.97 | 94.95 | 89.90 |
|  | R22-derived yield (%) | TFE | 44.15 | 45.06 | 48.81 | 62.47 | 60.95 | 64.62 | 71.99 | 29.23 |
|  |  | HFO-1234yf | 13.67 | 13.36 | 12.82 | 9.46 | 9.79 | 8.12 | 4.68 | 10.25 |
|  |  | VdF | 33.18 | 30.35 | 26.75 | 15.80 | 17.04 | 13.06 | 7.18 | 39.90 |
|  |  | HFP | 1.11 | 1.24 | 1.35 | 1.82 | 2.01 | 1.96 | 2.83 | 0.00 |
|  |  | Trifluoroethylene | 1.61 | 1.11 | 0.76 | 0.39 | 0.51 | 0.41 | 0.43 | 1.09 |
|  |  | CTFE | 0.69 | 0.82 | 0.90 | 1.03 | 1.11 | 1.03 | 1.11 | 0.42 |
|  |  | RC318 | 0.69 | 0.90 | 1.21 | 2.34 | 2.37 | 2.61 | 3.52 | 0.17 |
|  |  | Others | 2.55 | 3.58 | 3.54 | 2.74 | 3.03 | 3.17 | 3.20 | 8.83 |
|  | R22-derived selectivity (%) | TFE | 45.21 | 46.73 | 50.77 | 65.04 | 62.95 | 68.04 | 75.82 | 32.51 |
|  |  | HFO-1234yf | 14.00 | 13.86 | 13.33 | 9.85 | 10.11 | 8.55 | 4.93 | 11.40 |
|  |  | VdF | 33.98 | 31.48 | 27.82 | 16.45 | 17.60 | 13.75 | 7.56 | 44.39 |
|  |  | HFP | 1.13 | 1.29 | 1.41 | 1.90 | 2.07 | 2.07 | 2.98 | 0.00 |
|  |  | Trifluoroethylene | 1.65 | 1.15 | 0.79 | 0.40 | 0.53 | 0.43 | 0.46 | 1.21 |
|  |  | CTFE | 0.71 | 0.85 | 0.94 | 1.08 | 1.15 | 1.09 | 1.17 | 0.47 |
|  |  | RC318 | 0.70 | 0.94 | 1.26 | 2.44 | 2.45 | 2.75 | 3.71 | 0.19 |
|  |  | Others | 2.61 | 3.71 | 3.68 | 2.85 | 3.13 | 3.34 | 3.37 | 9.82 |

Examples 12 to 16

The reaction was conducted under the same conditions as in Example 5 except that the molar ratio (R40/R22) in the raw material gas in the reactor, the retention time and the gas temperature of R40 were changed as shown in Table 3. Then, the gas of a reaction mixture withdrawn from the outlet of the reactor was treated in the same manner as in Example 1, and then, the obtained outlet gas was analyzed in the same manner as in Example 1. The results are shown in Table 3 together with the reaction conditions.

TABLE 3

|  |  | Example No. | | | | |
|---|---|---|---|---|---|---|
|  |  | Ex. 12 | Ex. 13 | Ex. 14 | Ex. 15 | Ex. 16 |
| Production conditions | Temperature (° C.) in reactor | 800 | 800 | 800 | 800 | 800 |
|  | Pressure (gauge pressure) (MPa) | 0.042 | 0.042 | 0.042 | 0.042 | 0.042 |

TABLE 3-continued

|  |  | Example No. | | | | |
|---|---|---|---|---|---|---|
|  |  | Ex. 12 | Ex. 13 | Ex. 14 | Ex. 15 | Ex. 16 |
|  | Retention time (s) | 3.0 | 1.5 | 1.0 | 0.75 | 0.3 |
|  | R40/R22 (molar ratio) | 0.5 | 0.5 | 0.5 | 0.5 | 0.5 |
|  | R40 temperature (° C.) | 600 | 600 | 600 | 600 | 300 |
|  | R22 temperature (° C.) | 300 | 300 | 300 | 300 | 300 |
|  | Heat medium (steam)/ (R40 + R22 + steam) × 100 (vol %) | 90 | 90 | 90 | 90 | 90 |
|  | Heat medium temperature (° C.) | 750 | 750 | 750 | 750 | 800 |
|  | Heat medium pressure (gauge pressure) (MPa) | 0.042 | 0.042 | 0.042 | 0.042 | 0.042 |
| Analytical results of reaction gas | Molar composition of outlet gas (mol %) TFE | 10.03 | 13.98 | 19.35 | 25.58 | 39.56 |
|  | VdF | 42.64 | 38.56 | 34.09 | 27.65 | 10.36 |
|  | HFP | 1.25 | 1.20 | 1.14 | 0.97 | 0.40 |
|  | Trifluoroethylene | 0.69 | 0.60 | 0.47 | 0.35 | 0.15 |
|  | RC318 | 0.16 | 0.24 | 0.37 | 0.50 | 0.49 |
|  | HFO-1234yf | 11.40 | 10.51 | 9.48 | 7.80 | 2.84 |
|  | R22 | 5.29 | 5.72 | 6.21 | 6.91 | 9.20 |
|  | CTFE | 1.00 | 1.03 | 0.99 | 0.86 | 0.30 |
|  | R40 | 23.15 | 23.46 | 23.98 | 26.28 | 35.27 |
|  | Others | 4.38 | 4.70 | 3.93 | 3.09 | 1.44 |
|  | Total | 100.0 | 100.0 | 100.0 | 100.0 | 100.0 |
|  | HFO-1234yf/VdF | 0.267 | 0.273 | 0.278 | 0.282 | 0.274 |
|  | R40 yield (%) | 29.33 | 31.49 | 34.72 | 41.72 | 71.79 |
|  | R40 conversion (=R40 reaction rate (%)) | 70.67 | 68.51 | 65.28 | 58.28 | 28.21 |
|  | R40-derived yield (%) HFO-1234yf | 14.45 | 14.11 | 13.73 | 12.38 | 5.79 |
|  | VdF | 54.02 | 51.76 | 49.35 | 43.89 | 21.10 |
|  | Others | 2.21 | 2.65 | 2.21 | 2.00 | 1.33 |
|  | R40-derived selectivity (%) HFO-1234yf | 20.44 | 20.59 | 21.03 | 21.24 | 20.52 |
|  | VdF | 76.44 | 75.55 | 75.59 | 75.32 | 74.78 |
|  | Others | 3.12 | 3.86 | 3.38 | 3.44 | 4.70 |
|  | R22 yield (%) | 4.99 | 5.22 | 5.49 | 6.05 | 8.29 |
|  | R22 conversion (=R22 reaction rate (%)) | 95.01 | 94.78 | 94.51 | 93.95 | 91.71 |
|  | R22-derived yield (%) TFE | 18.89 | 25.52 | 34.25 | 44.77 | 71.33 |
|  | HFO-1234yf | 21.48 | 19.18 | 16.79 | 13.65 | 5.13 |
|  | VdF | 40.16 | 35.19 | 30.17 | 24.20 | 9.35 |
|  | HFP | 3.52 | 3.28 | 3.02 | 2.54 | 1.09 |
|  | Trifluoroethylene | 1.30 | 1.09 | 0.83 | 0.61 | 0.26 |
|  | CTFE | 1.89 | 1.87 | 1.76 | 1.51 | 0.53 |
|  | RC318 | 0.59 | 0.88 | 1.29 | 1.74 | 1.76 |
|  | Others | 7.17 | 7.78 | 6.40 | 4.92 | 2.26 |
|  | R22-derived selectivity (%) TFE | 19.89 | 26.92 | 36.24 | 47.66 | 77.78 |
|  | HFO-1234yf | 22.61 | 20.24 | 17.76 | 14.53 | 5.59 |
|  | VdF | 42.27 | 37.12 | 31.93 | 25.76 | 10.19 |
|  | HFP | 3.71 | 3.46 | 3.19 | 2.70 | 1.19 |
|  | Trifluoroethylene | 1.37 | 1.16 | 0.88 | 0.65 | 0.29 |
|  | CTFE | 1.99 | 1.97 | 1.86 | 1.61 | 0.58 |
|  | RC318 | 0.62 | 0.92 | 1.37 | 1.86 | 1.92 |
|  | Others | 7.55 | 8.21 | 6.77 | 5.24 | 2.46 |

Examples 17 to 22

The reaction was conducted under the same conditions as in Example 5 except that the molar ratio (R40/R22) and the gas temperatures of R40 and R22 were changed as shown in Table 4. Then, the gas of a reaction mixture withdrawn from the outlet of the reactor was treated in the same manner as in Example 1, and then, the obtained outlet gas was analyzed in the same manner as in Example 1. The results are shown in Table 4 together with the reaction conditions.

TABLE 4

|  |  | Example No. | | | | | |
|---|---|---|---|---|---|---|---|
|  |  | Ex. 17 | Ex. 18 | Ex. 19 | Ex. 20 | Ex. 21 | Ex. 22 |
| Production conditions | Temperature (° C.) in reactor | 800 | 800 | 800 | 800 | 800 | 800 |
|  | Pressure (gauge pressure) (MPa) | 0.042 | 0.042 | 0.042 | 0.042 | 0.042 | 0.042 |
|  | Retention time (s) | 0.5 | 0.5 | 0.5 | 0.5 | 0.5 | 0.5 |
|  | R40/R22 (molar ratio) | 0.5 | 0.5 | 0.5 | 0.5 | 0.5 | 0.5 |
|  | R40 temperature (° C.) | 10 | 300 | 500 | 600 | 700 | 800 |
|  | R22 temperature (° C.) | 10 | 300 | 300 | 300 | 300 | 300 |
|  | Heat medium (steam)/ (R40 + R22 + steam) × 100 (vol %) | 90 | 90 | 90 | 90 | 90 | 90 |
|  | Heat medium temperature (° C.) | 800 | 800 | 800 | 800 | 800 | 800 |

TABLE 4-continued

| | | | Example No. | | | | | |
|---|---|---|---|---|---|---|---|---|
| | | | Ex. 17 | Ex. 18 | Ex. 19 | Ex. 20 | Ex. 21 | Ex. 22 |
| | Heat medium pressure (gauge pressure) (MPa) | | 0.042 | 0.042 | 0.042 | 0.042 | 0.042 | 0.042 |
| Analytical results of reaction gas | Molar composition of outlet gas (mol %) | TFE | 36.05 | 33.74 | 33.52 | 32.82 | 32.86 | 31.03 |
| | | VdF | 19.40 | 20.75 | 21.03 | 21.44 | 22.34 | 25.73 |
| | | HFP | 0.77 | 0.77 | 0.79 | 0.77 | 0.79 | 0.87 |
| | | Trifluoroethylene | 0.25 | 0.28 | 0.27 | 0.28 | 0.29 | 0.50 |
| | | RC318 | 0.66 | 0.61 | 0.60 | 0.59 | 0.59 | 0.54 |
| | | HFO-1234yf | 5.61 | 5.81 | 5.83 | 5.90 | 6.17 | 6.63 |
| | | R22 | 6.88 | 6.23 | 6.71 | 7.32 | 7.33 | 7.69 |
| | | CTFE | 0.66 | 0.67 | 0.69 | 0.70 | 0.73 | 0.76 |
| | | R40 | 27.15 | 28.71 | 28.06 | 27.46 | 25.68 | 20.62 |
| | | Others | 2.55 | 2.44 | 2.51 | 2.72 | 3.21 | 5.63 |
| | | Total | 100.0 | 100.0 | 100.0 | 100.0 | 100.0 | 100.0 |
| | | HFO-1234yf/VdF | 0.289 | 0.280 | 0.277 | 0.275 | 0.276 | 0.258 |
| | R40 yield (%) | | 50.97 | 50.88 | 49.99 | 48.89 | 45.93 | 36.56 |
| | R40 conversion (=R40 reaction rate (%)) | | 49.03 | 49.12 | 50.01 | 51.11 | 54.07 | 63.44 |
| | R40-derived yield (%) | HFO-1234yf | 10.53 | 10.29 | 10.39 | 10.51 | 11.04 | 11.76 |
| | | VdF | 36.43 | 36.78 | 37.47 | 38.16 | 39.96 | 45.63 |
| | | Others | 2.07 | 2.05 | 2.15 | 2.44 | 3.07 | 6.05 |
| | R40-derived selectivity (%) | HFO-1234yf | 21.48 | 20.95 | 20.78 | 20.56 | 20.41 | 18.54 |
| | | VdF | 74.29 | 74.88 | 74.92 | 74.67 | 73.91 | 71.92 |
| | | Others | 4.23 | 4.17 | 4.30 | 4.77 | 5.68 | 9.54 |
| | R22 yield (%) | | 5.70 | 5.32 | 5.71 | 6.24 | 6.14 | 6.23 |
| | R22 conversion (=R22 reaction rate (%)) | | 94.30 | 94.68 | 94.29 | 93.76 | 93.86 | 93.77 |
| | R22-derived yield (%) | TFE | 59.76 | 57.68 | 57.06 | 55.92 | 55.01 | 50.29 |
| | | HFO-1234yf | 9.30 | 9.93 | 9.93 | 10.06 | 10.33 | 10.75 |
| | | VdF | 16.08 | 17.73 | 17.90 | 18.26 | 18.70 | 20.86 |
| | | HFP | 1.91 | 1.98 | 2.02 | 1.97 | 1.99 | 2.11 |
| | | Trifluoroethylene | 0.42 | 0.47 | 0.46 | 0.47 | 0.49 | 0.81 |
| | | CTFE | 1.10 | 1.15 | 1.17 | 1.19 | 1.21 | 1.23 |
| | | RC318 | 2.20 | 2.07 | 2.05 | 2.01 | 1.97 | 1.76 |
| | | Others | 3.51 | 3.67 | 3.71 | 3.89 | 4.16 | 5.96 |
| | R22-derived selectivity (%) | TFE | 63.38 | 60.92 | 60.51 | 59.64 | 58.60 | 53.63 |
| | | HFO-1234yf | 9.86 | 10.48 | 10.53 | 10.73 | 11.00 | 11.47 |
| | | VdF | 17.06 | 18.73 | 18.98 | 19.48 | 19.92 | 22.24 |
| | | HFP | 2.03 | 2.09 | 2.14 | 2.10 | 2.12 | 2.25 |
| | | Trifluoroethylene | 0.44 | 0.50 | 0.48 | 0.50 | 0.53 | 0.86 |
| | | CTFE | 1.17 | 1.22 | 1.24 | 1.27 | 1.29 | 1.31 |
| | | RC318 | 2.34 | 2.19 | 2.17 | 2.14 | 2.10 | 1.88 |
| | | Others | 3.72 | 3.88 | 3.93 | 4.15 | 4.43 | 6.36 |

Examples 23 to 30

The reaction was conducted under the same conditions as in Example 5 except that the temperature in the reactor, the retention time of the raw material gas, the molar ratio of R40/R22 and the gas temperature of R40 were changed as shown in Table 5. Then, the gas of a reaction mixture withdrawn from the outlet of the reactor was treated in the same manner as in Example 1, and then, the obtained outlet gas was analyzed in the same manner as in Example 1. The results are shown in Table 5 together with the reaction conditions.

TABLE 5

| | | Example No. | | | | | | | |
|---|---|---|---|---|---|---|---|---|---|
| | | Ex. 23 | Ex. 24 | Ex. 25 | Ex. 26 | Ex. 27 | Ex. 28 | Ex. 29 | Ex. 30 |
| Production conditions | Temperature (° C.) in reactor | 860 | 860 | 830 | 830 | 770 | 770 | 740 | 710 |
| | Pressure (gauge pressure) (MPa) | 0.042 | 0.042 | 0.042 | 0.042 | 0.042 | 0.042 | 0.042 | 0.042 |
| | Retention time (s) | 0.3 | 0.5 | 0.25 | 1.0 | 0.5 | 0.5 | 0.5 | 0.5 |
| | R40/R22 (molar ratio) | 0.5 | 0.5 | 0.5 | 0.5 | 0.5 | 0.5 | 0.5 | 0.5 |
| | R40 temperature (° C.) | 600 | 600 | 300 | 300 | 600 | 300 | 300 | 300 |
| | R22 temperature (° C.) | 300 | 300 | 300 | 300 | 300 | 300 | 300 | 300 |
| | Heat medium (steam)/(R40 + R22 + steam) × 100 (vol %) | 90 | 90 | 90 | 90 | 90 | 90 | 90 | 90 |
| | Heat medium temperature (° C.) | 880 | 880 | 750 | 750 | 750 | 750 | 750 | 750 |
| | Heat medium pressure (gauge pressure) (MPa) | 0.042 | 0.042 | 0.042 | 0.042 | 0.042 | 0.042 | 0.042 | 0.042 |

TABLE 5-continued

| | | | Ex. 23 | Ex. 24 | Ex. 25 | Ex. 26 | Ex. 27 | Ex. 28 | Ex. 29 | Ex. 30 |
|---|---|---|---|---|---|---|---|---|---|---|
| Analytical results of reaction gas | Molar composition of outlet gas (mol %) | TFE | 23.23 | 7.83 | 39.36 | 10.66 | 44.32 | 43.27 | 44.15 | 38.25 |
| | | VdF | 35.85 | 56.97 | 14.22 | 45.89 | 9.92 | 8.93 | 4.32 | 2.53 |
| | | HFP | 1.50 | 1.35 | 0.62 | 1.57 | 0.47 | 0.43 | 0.24 | 0.12 |
| | | Trifluoroethylene | 0.75 | 1.35 | 0.32 | 1.45 | 0.16 | 0.13 | 0.07 | 0.04 |
| | | RC318 | 0.21 | 0.01 | 0.55 | 0.11 | 0.86 | 0.83 | 0.65 | 0.34 |
| | | HFO-1234yf | 5.87 | 8.34 | 3.75 | 9.96 | 3.45 | 3.20 | 1.45 | 0.74 |
| | | R22 | 6.58 | 3.79 | 3.04 | 2.23 | 7.45 | 7.68 | 12.07 | 21.28 |
| | | CTFE | 1.01 | 1.39 | 0.21 | 0.67 | 0.34 | 0.32 | 0.14 | 0.04 |
| | | R40 | 20.27 | 13.09 | 36.15 | 21.96 | 30.91 | 33.68 | 35.86 | 35.88 |
| | | Others | 4.73 | 5.87 | 1.79 | 5.50 | 2.13 | 1.52 | 1.04 | 0.79 |
| | | Total | 100.0 | 100.0 | 100.0 | 100.0 | 100.0 | 100.0 | 100.0 | 100.0 |
| | | HFO-1234yf/VdF | 0.164 | 0.146 | 0.263 | 0.217 | 0.347 | 0.358 | 0.336 | 0.291 |
| R40 yield (%) | | | 31.51 | 16.08 | 65.67 | 27.4 | 68.16 | 72.47 | 85.1 | 90.8 |
| R40 conversion (=R40 reaction rate (%)) | | | 68.49 | 83.92 | 34.33 | 72.6 | 31.84 | 27.53 | 14.9 | 9.2 |
| R40-derived yield (%) | | HFO-1234yf | 9.13 | 10.24 | 6.81 | 12.4 | 7.60 | 6.88 | 3.4 | 1.9 |
| | | VdF | 55.72 | 69.97 | 25.84 | 57.2 | 21.87 | 19.22 | 10.3 | 6.4 |
| | | Others | 3.65 | 3.70 | 1.68 | 3.0 | 2.38 | 1.43 | 1.2 | 0.9 |
| R40-derived selectivity (%) | | HFO-1234yf | 13.33 | 12.21 | 19.83 | 17.1 | 23.86 | 24.98 | 23.2 | 20.3 |
| | | VdF | 81.35 | 83.38 | 75.26 | 78.8 | 68.68 | 69.83 | 69.0 | 69.8 |
| | | Others | 5.33 | 4.41 | 4.91 | 4.1 | 7.46 | 5.19 | 7.8 | 9.9 |
| R22 yield (%) | | | 5.58 | 3.35 | 2.72 | 2.1 | 6.12 | 6.53 | 10.7 | 20.3 |
| R22 conversion (=R22 reaction rate (%)) | | | 94.42 | 96.65 | 97.28 | 97.9 | 93.88 | 93.47 | 89.3 | 79.7 |
| R22-derived yield (%) | | TFE | 39.43 | 13.86 | 70.45 | 19.6 | 72.86 | 73.60 | 78.1 | 72.9 |
| | | HFO-1234yf | 9.97 | 14.76 | 6.71 | 18.3 | 5.66 | 5.44 | 2.6 | 1.4 |
| | | VdF | 30.43 | 50.41 | 12.73 | 42.1 | 8.15 | 7.60 | 3.8 | 2.4 |
| | | HFP | 3.81 | 3.57 | 1.67 | 4.3 | 1.17 | 1.10 | 0.6 | 0.3 |
| | | Trifluoroethylene | 1.26 | 2.39 | 0.57 | 2.7 | 0.27 | 0.22 | 0.1 | 0.1 |
| | | CTFE | 1.72 | 2.45 | 0.37 | 1.2 | 0.56 | 0.55 | 0.2 | 0.1 |
| | | RC318 | 0.72 | 0.05 | 1.98 | 0.4 | 2.82 | 2.84 | 2.3 | 1.3 |
| | | Others | 7.08 | 9.15 | 2.82 | 9.3 | 2.39 | 2.13 | 1.5 | 1.2 |
| R22-derived selectivity (%) | | TFE | 41.76 | 14.34 | 72.42 | 20.0 | 77.61 | 78.74 | 87.5 | 91.5 |
| | | HFO-1234yf | 10.56 | 15.27 | 6.89 | 18.7 | 6.03 | 5.82 | 2.9 | 1.8 |
| | | VdF | 32.23 | 52.16 | 13.08 | 43.0 | 8.68 | 8.13 | 4.3 | 3.0 |
| | | HFP | 4.03 | 3.70 | 1.72 | 4.4 | 1.24 | 1.18 | 0.7 | 0.4 |
| | | Trifluoroethylene | 1.34 | 2.47 | 0.58 | 2.7 | 0.29 | 0.24 | 0.1 | 0.1 |
| | | CTFE | 1.82 | 2.54 | 0.38 | 1.2 | 0.60 | 0.59 | 0.3 | 0.1 |
| | | RC318 | 0.76 | 0.05 | 2.03 | 0.4 | 3.00 | 3.04 | 2.6 | 1.6 |
| | | Others | 7.50 | 9.47 | 2.90 | 9.5 | 2.55 | 2.27 | 1.6 | 1.5 |

Examples 31 to 36

The reaction was conducted under the same conditions as in Example 5 except that the gas temperature of R40, the molar ratio of R40/R22 and the supply proportion (vol %) of steam to the entire gas supply amount (the proportion represented by a volume ratio of steam/(R40+R22+ steam)) were changed as shown in Table 6. Then, the gas of a reaction mixture withdrawn from the outlet of the reactor was treated in the same manner as in Example 1, and then, the obtained outlet gas was analyzed in the same manner as in Example 1. The results are shown in Table 6 together with the reaction conditions.

TABLE 6

| | | | Ex. 31 | Ex. 32 | Ex. 33 | Ex. 34 | Ex. 35 | Ex. 36 |
|---|---|---|---|---|---|---|---|---|
| Production conditions | | Temperature (° C.) in reactor | 800 | 800 | 800 | 800 | 800 | 800 |
| | | Pressure (gauge pressure) (MPa) | 0.042 | 0.042 | 0.042 | 0.042 | 0.042 | 0.042 |
| | | Retention time (s) | 0.5 | 0.5 | 0.5 | 0.5 | 0.5 | 0.5 |
| | | R40/R22 (molar ratio) | 0.5 | 0.5 | 0.5 | 0.5 | 0.5 | 0.5 |
| | | R40 temperature (° C.) | 300 | 300 | 300 | 300 | 300 | 300 |
| | | R22 temperature (° C.) | 300 | 300 | 300 | 300 | 300 | 300 |
| | | Heat medium (steam)/(R40 + R22 + steam) × 100 (vol %) | 88 | 83 | 80 | 75 | 67 | 50 |
| | | Heat medium temperature (° C.) | 750 | 750 | 750 | 750 | 800 | 800 |
| | | Heat medium pressure (gauge pressure) (MPa) | 0.042 | 0.042 | 0.042 | 0.042 | 0.042 | 0.042 |
| Analytical results of | Molar composition of | TFE | 33.93 | 31.90 | 28.83 | 26.67 | 25.56 | 21.18 |
| | | VdF | 18.87 | 17.08 | 18.38 | 21.49 | 19.72 | 19.76 |

TABLE 6-continued

| | | | Example No. | | | | | |
|---|---|---|---|---|---|---|---|---|
| | | | Ex. 31 | Ex. 32 | Ex. 33 | Ex. 34 | Ex. 35 | Ex. 36 |
| reaction gas | outlet gas (mol %) | HFP | 0.74 | 0.88 | 1.11 | 1.23 | 1.19 | 1.23 |
| | | Trifluoroethylene | 0.25 | 0.25 | 0.27 | 0.34 | 0.33 | 0.35 |
| | | RC318 | 0.77 | 0.88 | 0.93 | 1.01 | 1.15 | 1.22 |
| | | HFO-1234yf | 6.02 | 6.10 | 6.73 | 7.63 | 7.35 | 7.48 |
| | | R22 | 8.61 | 9.77 | 10.20 | 10.33 | 11.87 | 14.60 |
| | | CTFE | 0.62 | 0.56 | 0.60 | 0.70 | 0.63 | 0.59 |
| | | R40 | 27.52 | 28.92 | 28.72 | 24.18 | 25.18 | 24.22 |
| | | Others | 2.69 | 3.67 | 4.21 | 6.40 | 7.02 | 9.37 |
| | | Total | 100.0 | 100.0 | 100.0 | 100.0 | 100.0 | 100.0 |
| | | HFO-1234yf/VdF | 0.319 | 0.357 | 0.366 | 0.355 | 0.373 | 0.378 |
| | R40 yield (%) | | 51.3 | 54.0 | 51.5 | 42.9 | 45.3 | 43.1 |
| | R40 conversion (=R40 reaction rate (%)) | | 48.7 | 46.0 | 48.5 | 57.1 | 54.7 | 56.9 |
| | R40-derived yield (%) | HFO-1234yf | 11.2 | 11.4 | 12.1 | 13.5 | 13.2 | 13.3 |
| | | VdF | 35.2 | 31.9 | 33.0 | 38.2 | 35.4 | 35.2 |
| | | Others | 2.3 | 2.8 | 3.4 | 5.4 | 6.1 | 8.5 |
| | R40-derived selectivity (%) | HFO-1234yf | 23.0 | 24.7 | 24.9 | 23.7 | 24.1 | 23.4 |
| | | VdF | 72.3 | 69.2 | 68.0 | 66.8 | 64.7 | 61.8 |
| | | Others | 4.7 | 6.1 | 7.0 | 9.4 | 11.1 | 14.9 |
| | R22 yield (%) | | 7.2 | 8.3 | 8.8 | 8.4 | 9.8 | 12.2 |
| | R22 conversion (=R22 reaction rate (%)) | | 92.8 | 91.7 | 91.2 | 91.6 | 90.2 | 87.8 |
| | R22-derived yield (%) | TFE | 56.9 | 54.3 | 49.5 | 43.6 | 42.3 | 35.3 |
| | | HFO-1234yf | 10.1 | 10.4 | 11.6 | 12.5 | 12.2 | 12.5 |
| | | VdF | 15.8 | 14.5 | 15.8 | 17.6 | 16.3 | 16.5 |
| | | HFP | 1.8 | 2.2 | 2.9 | 3.0 | 3.0 | 3.1 |
| | | Trifluoroethylene | 0.4 | 0.4 | 0.5 | 0.6 | 0.5 | 0.6 |
| | | CTFE | 1.0 | 1.0 | 1.0 | 1.1 | 1.0 | 1.0 |
| | | RC318 | 2.6 | 3.0 | 3.2 | 3.3 | 3.8 | 4.1 |
| | | Others | 4.1 | 5.9 | 6.8 | 9.9 | 11.0 | 14.9 |
| | R22-derived selectivity (%) | TFE | 61.3 | 59.2 | 54.3 | 47.6 | 46.9 | 40.2 |
| | | HFO-1234yf | 10.9 | 11.3 | 12.7 | 13.6 | 13.5 | 14.2 |
| | | VdF | 17.0 | 15.9 | 17.3 | 19.2 | 18.1 | 18.8 |
| | | HFP | 2.0 | 2.4 | 3.1 | 3.3 | 3.3 | 3.5 |
| | | Trifluoroethylene | 0.4 | 0.5 | 0.5 | 0.6 | 0.6 | 0.7 |
| | | CTFE | 1.1 | 1.0 | 1.1 | 1.2 | 1.2 | 1.1 |
| | | RC318 | 2.8 | 3.3 | 3.5 | 3.6 | 4.2 | 4.6 |
| | | Others | 4.5 | 6.4 | 7.5 | 10.8 | 12.2 | 16.9 |

Examples 37 to 39

The reaction was conducted under the same conditions as in Example 5 except that the gas temperature of R40, the molar ratio of R40/R22 and the pressure in the reactor were changed as shown in Table 7. Then, the gas of a reaction mixture withdrawn from the outlet of the reactor was treated in the same manner as in Example 1, and then, the obtained outlet gas was analyzed in the same manner as in Example 1. The results are shown in Table 7 together with the reaction conditions.

TABLE 7

| | Example No. | | Ex. 37 | Ex. 38 | Ex. 39 |
|---|---|---|---|---|---|
| Production conditions | Temperature (° C.) in reactor | | 800 | 800 | 800 |
| | Pressure (gauge pressure) (MPa) | | 0.009 | 0.068 | 0.098 |
| | Retention time (s) | | 0.5 | 0.5 | 0.5 |
| | R40/R22 (molar ratio) | | 0.5 | 0.5 | 0.5 |
| | R40 temperature (° C.) | | 300 | 300 | 300 |
| | R22 temperature (° C.) | | 300 | 300 | 300 |
| | Heat medium (steam)/(R40 + R22 + steam) × 100 (vol %) | | 90 | 90 | 90 |
| | Heat medium temperature (° C.) | | 750 | 750 | 750 |
| | Heat medium pressure (gauge pressure) (MPa) | | 0.009 | 0.068 | 0.098 |

TABLE 7-continued

| | Example No. | | Ex. 37 | Ex. 38 | Ex. 39 |
|---|---|---|---|---|---|
| Analytical results of reaction gas | Molar composition of outlet gas (mol %) | TFE | 38.82 | 30.82 | 26.60 |
| | | VdF | 15.84 | 23.42 | 27.00 |
| | | HFP | 0.61 | 0.88 | 0.99 |
| | | Trifluoroethylene | 0.21 | 0.35 | 0.42 |
| | | RC318 | 0.49 | 0.67 | 0.68 |
| | | HFO-1234yf | 3.94 | 6.97 | 8.23 |
| | | R22 | 6.37 | 7.49 | 7.66 |
| | | CTFE | 0.52 | 0.79 | 0.89 |
| | | R40 | 30.59 | 24.73 | 23.02 |
| | | Others | 2.61 | 3.86 | 4.50 |
| | | Total | 100.0 | 100.0 | 100.0 |
| | | HFO-1234yf/VdF | 0.249 | 0.298 | 0.305 |
| | R40 yield (%) | | 58.9 | 43.4 | 38.1 |
| | R40 conversion (=R40 reaction rate (%)) | | 41.1 | 56.6 | 61.9 |
| | R40-derived yield (%) | HFO-1234yf | 7.6 | 12.2 | 13.6 |
| | | VdF | 30.5 | 41.1 | 44.7 |
| | | Others | 3.0 | 3.3 | 3.6 |
| | R40-derived selectivity (%) | HFO-1234yf | 18.5 | 21.6 | 22.0 |
| | | VdF | 74.2 | 72.5 | 72.2 |
| | | Others | 7.3 | 5.9 | 5.8 |
| | R22 yield (%) | | 5.4 | 6.2 | 6.3 |
| | R22 conversion (=R22 reaction rate (%)) | | 94.6 | 93.8 | 93.7 |
| | R22-derived yield (%) | TFE | 66.0 | 50.9 | 44.0 |
| | | HFO-1234yf | 6.7 | 11.5 | 13.6 |

TABLE 7-continued

| Example No. | | Ex. 37 | Ex. 38 | Ex. 39 |
|---|---|---|---|---|
| | VdF | 13.5 | 19.3 | 22.4 |
| | HFP | 1.5 | 2.2 | 2.5 |
| | Trifluoro-ethylene | 0.4 | 0.6 | 0.7 |
| | CTFE | 0.9 | 1.3 | 1.5 |
| | RC318 | 1.7 | 2.2 | 2.2 |
| | Others | 4.0 | 5.8 | 6.7 |
| R22-derived selectivity (%) | TFE | 69.8 | 54.2 | 47.0 |
| | HFO-1234yf | 7.1 | 12.3 | 14.6 |
| | VdF | 14.2 | 20.6 | 23.9 |
| | HFP | 1.6 | 2.3 | 2.6 |
| | Trifluoro-ethylene | 0.4 | 0.6 | 0.7 |
| | CTFE | 0.9 | 1.4 | 1.6 |
| | RC318 | 1.8 | 2.4 | 2.4 |
| | Others | 4.2 | 6.2 | 7.2 |

As is evident from Tables 1 to 7, in each of Examples 1 to 39, the value of HFO-1234yf/VdF in the outlet gas is at least 0.14, and the selectivity (%) of HFO-1234yf derived from R40 is distinctly high as compared with the same in Comparative Examples 1 to 3 wherein R40/R22 is outside the range of the present invention. Especially, the value of HFO-1234yf/VdF in the outlet gas is at least 0.17 in Examples 2 to 22 and 25 to 39, and further, is at least 0.2 in Examples 3 to 22 and 25 to 39.

These results indicate that according to the process of the present invention, HFO-1234yf can be obtained efficiently.

Further, in each Example under the above reaction conditions, it has been confirmed that in the reaction under the same conditions, substantially the same results are obtainable with good reproducibility. Thus, it can be said that according to the process of the present invention, control of the reaction conditions is easy, and accordingly, quantitative production of HFO-1234yf is possible.

INDUSTRIAL APPLICABILITY

According to the process of the present invention, it is possible to produce industrially useful HFO-1234yf efficiently by using readily available R22 and R40 as raw material and reacting them as they are without taking out an intermediate product from the reaction system. Thus, as compared with conventional methods, it is possible to substantially reduce costs required for the raw material and production facilities.

Further, according to the process of the present invention, control of the production (reaction) conditions is easy, whereby quantitative production of HFO-1234yf becomes possible, and economical merits are substantial. Specifically, it is economically advantageous that in the synthetic reaction involving thermal decomposition using R22 and R40 as raw material, the proportion of HFO-1234yf in the reaction mixture can be made to be at least a certain value in a relative relation to VdF, of which the content proportion tends to be high in the reaction mixture. Furthermore, recycling of byproducts is also possible, whereby economical effects are substantial.

This application is a continuation of PCT Application No. PCT/JP2013/057257, filed on Mar. 14, 2013, which is based upon and claims the benefit of priority from Japanese Patent Application No. 2012-057568 filed on Mar. 14, 2012 and Japanese Patent Application No. 2012-169497 filed on Jul. 31, 2012. The contents of those applications are incorporated herein by reference in their entireties.

REFERENCE SYMBOLS

1: reactor, 2: supply line for R40, 3: supply line for R22, 4: supply line for steam, 2a, 3a: preheater, 4a: super-heated steam generator, 6: cooling means, 7: outlet line, 8: steam and acidic liquid-recovery tank, 9: alkaline cleaning device, 10: dehydrating tower, 20: reaction apparatus

What is claimed is:

1. A process for producing 2,3,3,3-tetrafluoropropene from chlorodifluoromethane and chloromethane, the process comprising:
    (a) supplying chlorodifluoromethane and chloromethane to a reactor, as preliminarily mixed or separately, in a molar ratio of chloromethane to chlorodifluoromethane of from 0.01 to 3,
    (b) supplying a heat medium to the reactor, and
    (c) contacting the heat medium with chlorodifluoromethane and chloromethane in the reactor to form 2,3,3,3-tetrafluoropropene.

2. The process according to claim 1, wherein the molar ratio of chloromethane to chlorodifluoromethane is from 0.01 to 1.5.

3. The process according to claim 1, wherein
    in said contacting (c), 1,1-difluoroethylene is further formed, and
    a molar ratio of 2,3,3,3-tetrafluoropropene to 1,1-difluoroethylene is at least 0.14.

4. The process according to claim 1, wherein a temperature in the reactor in said contacting (c) is adjusted to be from 400 to 1,200° C.

5. The process according to claim 4, wherein the temperature in the reactor is adjusted to be from 600 to 900° C.

6. The process according to claim 4, wherein the temperature in the reactor is adjusted to be from 710 to 830° C.

7. The process according to claim 1, wherein chloromethane is supplied to the reactor at a temperature of from 0 to 1,200° C.

8. The process according to claim 7, wherein the temperature of chloromethane supplied to the reactor is from 100 to 600° C.

9. The process for producing 2,3,3,3-tetrafluoropropene according to claim 1, wherein chlorodifluoromethane is supplied to the reactor at a temperature of from 0 to 600° C.

10. The process according to claim 9, wherein the temperature of chlorodifluoromethane supplied to the reactor is from 100 to 500° C.

11. The process according to claim 1, wherein the heat medium is at least one selected from the group consisting of steam, nitrogen and carbon dioxide.

12. The process according to claim 1, wherein the heat medium is supplied to the reactor at a temperature of from 100 to 1,200° C.

13. The process according to claim 1, wherein the heat medium is supplied to the reactor at an amount of from 20 to 98 vol % in an entire gas supplied to the reactor.

14. The process according to claim 1, wherein a contact time of the heat medium with chlorodifluoromethane and chloromethane in said contacting (c) is from 0.01 to 10 seconds.

15. The process according to claim 1, further comprising:
    (d) after said contacting (c), withdrawing from the reactor a reaction mixture comprising 2,3,3,3-tetrafluoropropene formed in the reactor,
    wherein said supplying (a), said supplying (b), and said withdrawing (d) are continuously carried out.

* * * * *